(12) United States Patent
Yuryev et al.

(10) Patent No.: US 11,395,717 B2
(45) Date of Patent: Jul. 26, 2022

(54) VISUALIZATION OF CLINICAL ORTHODONTIC ASSETS AND OCCLUSION CONTACT SHAPE

(71) Applicant: Align Technology, Inc., San Jose, CA (US)

(72) Inventors: Konstantin Yuryev, Moscow (RU); Vasily Stavenko, Moscow (RU); Andrey Verizhnikov, Moscow (RU)

(73) Assignee: Align Technology, Inc., San Jose, CA (US)

( * ) Notice: Subject to any disclaimer, the term of this patent is extended or adjusted under 35 U.S.C. 154(b) by 342 days.

(21) Appl. No.: 16/457,733

(22) Filed: Jun. 28, 2019

(65) Prior Publication Data

US 2020/0000555 A1     Jan. 2, 2020

Related U.S. Application Data

(60) Provisional application No. 62/692,513, filed on Jun. 29, 2018.

(51) Int. Cl.
| | |
|---|---|
| *G06K 9/00* | (2022.01) |
| *A61C 7/00* | (2006.01) |
| *G16H 50/50* | (2018.01) |
| *A61C 7/08* | (2006.01) |
| *G06T 19/00* | (2011.01) |
| *G06T 17/10* | (2006.01) |
| *A61C 9/00* | (2006.01) |

(52) U.S. Cl.
CPC .............. *A61C 7/002* (2013.01); *A61C 7/08* (2013.01); *G06T 17/10* (2013.01); *G06T 19/00* (2013.01); *G16H 50/50* (2018.01); *A61C 9/0053* (2013.01); *G06T 2219/004* (2013.01)

(58) Field of Classification Search
CPC ........... A61C 7/002; A61C 7/00; A61C 19/05; G06T 19/20; G06T 2207/30036; G06T 17/00; G06K 2209/40
See application file for complete search history.

(56) References Cited

U.S. PATENT DOCUMENTS

| | | |
|---|---|---|
| 5,975,893 A | 11/1999 | Chishti et al. |
| 6,227,850 B1 | 5/2001 | Chishti et al. |
| 6,227,851 B1 | 5/2001 | Chishti et al. |
| 6,299,440 B1 | 10/2001 | Phan et al. |
| 6,318,994 B1 | 11/2001 | Chishti et al. |
| 6,371,761 B1 | 4/2002 | Cheang et al. |
| 6,386,878 B1 | 5/2002 | Pavlovskaia et al. |
| 6,406,292 B1 | 6/2002 | Chishti et al. |
| 6,409,504 B1 | 6/2002 | Jones et al. |
| 6,457,972 B1 | 10/2002 | Chishti et al. |
| 6,488,499 B1 | 12/2002 | Miller |
| 6,514,074 B1 | 2/2003 | Chishti et al. |
| 6,554,611 B2 | 4/2003 | Chishti et al. |
| 6,582,229 B1 | 6/2003 | Miller et al. |
| 6,602,070 B2 | 8/2003 | Miller et al. |

(Continued)

*Primary Examiner* — Guillermo M Rivera-Martinez
(74) *Attorney, Agent, or Firm* — Shay Glenn LLP

(57) ABSTRACT

Methods of representing user edits or modifications of a treatment plan for a dental apparatus (e.g., one or a series of aligners) by managing an original clinical data set and a set of modifications of the clinical data set. Also described herein are methods of displaying, condensing, storing and reconstructing collision regions between two or more teeth.

15 Claims, 5 Drawing Sheets

(56) References Cited

U.S. PATENT DOCUMENTS

| | | |
|---|---|---|
| 6,621,491 B1 | 9/2003 | Baumrind et al. |
| 6,688,886 B2 | 2/2004 | Hughes et al. |
| 6,726,478 B1 | 4/2004 | Isiderio et al. |
| 6,729,876 B2 | 5/2004 | Chishti et al. |
| 6,739,869 B1 | 5/2004 | Taub et al. |
| 6,767,208 B2 | 7/2004 | Kaza |
| 6,783,360 B2 | 8/2004 | Chishti |
| 7,040,896 B2 | 5/2006 | Pavlovskaia et al. |
| 7,063,532 B1 | 6/2006 | Jones et al. |
| 7,074,038 B1 | 7/2006 | Miller |
| 7,074,039 B2 | 7/2006 | Kopelman et al. |
| 7,077,647 B2 | 7/2006 | Choi et al. |
| 7,108,508 B2 | 9/2006 | Hedge et al. |
| 7,134,874 B2 | 11/2006 | Chishti et al. |
| 7,156,661 B2 | 1/2007 | Choi et al. |
| 7,160,107 B2 | 1/2007 | Kopelman et al. |
| 7,241,142 B2 | 7/2007 | Abolfathi et al. |
| 7,293,988 B2 | 11/2007 | Wen |
| 7,309,230 B2 | 12/2007 | Wen |
| 7,357,634 B2 | 4/2008 | Knopp |
| 7,555,403 B2 | 6/2009 | Kopelman et al. |
| 7,637,740 B2 | 12/2009 | Knopp |
| 7,689,398 B2 | 3/2010 | Cheng et al. |
| 7,736,147 B2 | 6/2010 | Kaza et al. |
| 7,746,339 B2 | 6/2010 | Matov et al. |
| 7,844,356 B2 | 11/2010 | Matov et al. |
| 7,844,429 B2 | 11/2010 | Matov et al. |
| 7,865,259 B2 | 1/2011 | Kuo et al. |
| 7,878,804 B2 | 2/2011 | Korytov et al. |
| 7,880,751 B2 | 2/2011 | Kuo et al. |
| 7,904,308 B2 | 3/2011 | Arnone et al. |
| 7,930,189 B2 | 4/2011 | Kuo |
| 7,942,672 B2 | 5/2011 | Kuo |
| 7,970,627 B2 | 6/2011 | Kuo et al. |
| 7,970,628 B2 | 6/2011 | Kuo et al. |
| 8,038,444 B2 | 10/2011 | Kitching et al. |
| 8,044,954 B2 | 10/2011 | Kitching et al. |
| 8,075,306 B2 | 12/2011 | Kitching et al. |
| 8,092,215 B2 | 1/2012 | Stone-Collonge et al. |
| 8,099,268 B2 | 1/2012 | Kitching et al. |
| 8,108,189 B2 | 1/2012 | Chelnokov et al. |
| 8,126,726 B2 | 2/2012 | Matov et al. |
| 8,260,591 B2 | 9/2012 | Kass et al. |
| 8,275,180 B2 | 9/2012 | Kuo |
| 8,401,826 B2 | 3/2013 | Cheng et al. |
| 8,439,672 B2 | 5/2013 | Matov et al. |
| 8,562,338 B2 | 10/2013 | Kitching et al. |
| 8,591,225 B2 | 11/2013 | Wu et al. |
| 8,788,285 B2 | 7/2014 | Kuo |
| 8,843,381 B2 | 9/2014 | Kuo et al. |
| 8,874,452 B2 | 10/2014 | Kuo |
| 8,896,592 B2 | 11/2014 | Boltunov et al. |
| 8,930,219 B2 | 1/2015 | Trosien et al. |
| 9,037,439 B2 | 5/2015 | Kuo et al. |
| 9,060,829 B2 | 6/2015 | Sterental et al. |
| 9,125,709 B2 | 9/2015 | Matty |
| 9,211,166 B2 | 12/2015 | Kuo et al. |
| 9,220,580 B2 | 12/2015 | Borovinskih et al. |
| 9,364,296 B2 | 6/2016 | Kuo |
| 9,375,300 B2 | 6/2016 | Matov et al. |
| 9,414,897 B2 | 8/2016 | Wu et al. |
| 9,492,245 B2 | 11/2016 | Sherwood et al. |
| 9,642,678 B2 | 5/2017 | Kuo |
| 10,248,883 B2 | 4/2019 | Borovinskih et al. |
| 10,342,638 B2 | 7/2019 | Kitching et al. |
| 10,463,452 B2 | 11/2019 | Matov et al. |
| 10,595,966 B2 | 3/2020 | Carrier, Jr. et al. |
| 10,617,489 B2 | 4/2020 | Grove et al. |
| 10,722,328 B2 | 7/2020 | Velazquez et al. |
| 10,758,322 B2 | 9/2020 | Pokotilov et al. |
| 10,779,718 B2 | 9/2020 | Meyer et al. |
| 10,792,127 B2 | 10/2020 | Kopelman et al. |
| 10,828,130 B2 | 11/2020 | Pokotilov et al. |
| 10,835,349 B2 | 11/2020 | Cramer et al. |
| 10,973,611 B2 | 4/2021 | Pokotilov et al. |
| 10,996,813 B2 | 5/2021 | Makarenkova et al. |
| 10,997,727 B2 | 5/2021 | Xue et al. |
| 11,020,205 B2 | 6/2021 | Li et al. |
| 11,020,206 B2 | 6/2021 | Shi et al. |
| 11,026,766 B2 | 6/2021 | Chekh et al. |
| 11,033,359 B2 | 6/2021 | Velazquez et al. |
| 11,071,608 B2 | 7/2021 | Derakhshan et al. |
| 11,096,763 B2 | 8/2021 | Akopov et al. |
| 11,116,605 B2 | 9/2021 | Nyukhtikov et al. |
| 11,147,652 B2 | 10/2021 | Mason et al. |
| 11,151,753 B2 | 10/2021 | Gao et al. |
| 2003/0008259 A1 | 1/2003 | Kuo et al. |
| 2003/0143509 A1 | 7/2003 | Kopelman et al. |
| 2003/0207227 A1 | 11/2003 | Abolfathi |
| 2004/0137400 A1 | 7/2004 | Chishti et al. |
| 2004/0152036 A1 | 8/2004 | Abolfathi |
| 2004/0197728 A1 | 10/2004 | Abolfathi et al. |
| 2004/0259049 A1 | 12/2004 | Kopelman et al. |
| 2005/0182654 A1 | 8/2005 | Abolfathi et al. |
| 2005/0244791 A1 | 11/2005 | Davis et al. |
| 2006/0024637 A1* | 2/2006 | Raby .................. A61C 7/146 433/24 |
| 2006/0127836 A1 | 6/2006 | Wen |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2008/0306724 A1 | 12/2008 | Kitching et al. |
| 2010/0009308 A1 | 1/2010 | Wen et al. |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0167243 A1 | 7/2010 | Spiridonov et al. |
| 2010/0223034 A1* | 9/2010 | Imgrund .................. A61C 7/00 703/1 |
| 2011/0269097 A1* | 11/2011 | Sporbert ............. A61C 9/0046 433/24 |
| 2013/0204599 A1 | 8/2013 | Matov et al. |
| 2016/0242870 A1 | 8/2016 | Matov et al. |
| 2016/0310235 A1 | 10/2016 | Derakhshan et al. |
| 2017/0273760 A1 | 9/2017 | Morton et al. |
| 2018/0168780 A1* | 6/2018 | Kopelman .......... G06K 9/6212 |
| 2018/0280118 A1 | 10/2018 | Cramer |
| 2019/0029784 A1 | 1/2019 | Moalem et al. |
| 2019/0053876 A1 | 2/2019 | Sterental et al. |
| 2019/0192259 A1 | 6/2019 | Kopelman et al. |
| 2019/0328487 A1 | 10/2019 | Levin et al. |
| 2019/0328488 A1 | 10/2019 | Levin et al. |
| 2019/0333622 A1 | 10/2019 | Levin et al. |
| 2019/0343601 A1 | 11/2019 | Roschin et al. |
| 2019/0365514 A1* | 12/2019 | Hasan .................. A61C 13/097 |
| 2020/0000552 A1 | 1/2020 | Mednikov et al. |
| 2020/0000554 A1 | 1/2020 | Makarenkova et al. |
| 2020/0085546 A1 | 3/2020 | Li et al. |
| 2020/0107915 A1 | 4/2020 | Roschin et al. |
| 2020/0155274 A1 | 5/2020 | Pimenov et al. |
| 2020/0214800 A1 | 7/2020 | Matov et al. |
| 2020/0268495 A1* | 8/2020 | Ryakhovsky .......... A61C 11/00 |
| 2020/0297458 A1 | 9/2020 | Roschin et al. |
| 2020/0306011 A1 | 10/2020 | Chekhonin et al. |
| 2020/0306012 A1 | 10/2020 | Roschin et al. |
| 2020/0315744 A1 | 10/2020 | Cramer |
| 2020/0360109 A1 | 11/2020 | Gao et al. |
| 2021/0073998 A1 | 3/2021 | Brown et al. |
| 2021/0134436 A1 | 5/2021 | Meyer et al. |
| 2021/0174477 A1 | 6/2021 | Shi et al. |

\* cited by examiner

119

Display a representation of an original clinical data for a subject's dentition
120

Receive modifications to the original clinical data, wherein the modifications comprise changes in one or more of tooth position and tooth orientation.
122

Receive modifications to a view state of the representation of the original clinical data, including adding or removing one or more treatment features
124

Form a 3D scene of the original clinical data modified by the modifications to the original clinical data
126

Render the modified clinical data as a 3D representation based on the 3D scene and view state
128

Display the 3D representation of the modified clinical data
130

Receive further modifications to the original clinical data after displaying the 3D representation of the modified clinical data and updating the 3D scene, view state and 3D representation of the modified clinical data after receiving the further modification of the original clinical data.
132

FIG. 1B

VISUALIZATION OF CLINICAL ORTHODONTIC ASSETS AND OCCLUSION CONTACT SHAPE

CROSS REFERENCE TO RELATED APPLICATIONS

This patent application claims priority to U.S. provisional patent application No. 62/692,513, titled "VISUALIZATION OF CLINICAL ORTHODONTIC ASSETS AND OCCLUSION CONTACT SHAPE," filed on Jun. 29, 2018, herein incorporated by reference in its entirety.

This application may be related to U.S. patent application Ser. No. 16/178,491, titled "AUTOMATIC TREATMENT PLANNING," filed on Nov. 1, 2018 and herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Orthodontic treatment planning using a series of subject-removable appliances to reposition the teeth.

BACKGROUND

Orthodontic and dental treatments using a series of subject-removable appliances (e.g., "aligners") are very useful for treating subjects, and in particular for treating malocclusions. Treatment planning is typically performed in conjunction with the dental professional (e.g., dentist, orthodontist, dental technician, etc.), by generating a model of the subject's teeth in a final configuration and then breaking the treatment plan into a number of intermediate stages (steps) corresponding to individual appliances that are worn sequentially. This process may be interactive, adjusting the staging and in some cases the final target position, based on constraints on the movement of the teeth and the dental professional's preferences. Once the final treatment plan is finalized, the series of aligners may be manufactured corresponding to the treatment planning.

This treatment planning process may include many manual steps that are complex and may require a high level of knowledge of orthodontic norms. Further, because the steps are performed in series, the process may require a substantial amount of time. Manual steps may include preparation of the model for digital planning, reviewing and modifying proposed treatment plans (including staging) and aligner features placement (which includes features placed either on a tooth or on an aligner itself). These steps may be performed before providing an initial treatment plan to a dental professional, who may then modify the plan further and send it back for additional processing to adjust the treatment plan, repeating (iterating) this process until a final treatment plan is completed and then provided to the subject.

The methods and apparatuses described herein may improve treatment planning, including potentially increasing the speed at which treatment plans may be completed, as well as providing greater choices and control to the dental professional, and allowing improved subject involvement in the treatment planning process.

SUMMARY OF THE DISCLOSURE

The present invention relates to methods of representing user (e.g., doctor) edits or modifications of a treatment plan for a dental apparatus (e.g., one or a series of aligners) by managing an original clinical data set and a set of modifications of the clinical data set. A rendering engine may be used to render a view state and 3D scene from this information in the context of a user interface.

For example, described herein are computer-implemented methods (e.g., for modifying or designing a orthodontic treatment plan) that include: displaying a representation of an original clinical data for a subject's dentition; receiving modifications to the original clinical data; receiving modifications to a view state of the representation of the original clinical data; forming a 3D scene of the original clinical data modified by the modifications to the original clinical data; rendering the modified clinical data as a 3D representation based on the 3D scene and view state; displaying the 3D representation of the modified clinical data; and receiving further modifications to the original clinical data after displaying the 3D representation of the modified clinical data and updating the 3D scene, view state and 3D representation of the modified clinical data after receiving the further modification of the original clinical data.

Displaying a representation of the original clinical data for a subject's dentition may include displaying a 3D representation. For example, displaying the representation of the original clinical data may comprise displaying treatment features on the representation of the original clinical data for the subject's dentition; this display may be in images of a 3D representation and may be manipulated to show different angles, zoomed in/out, panned, etc.

Receiving modifications to the view state of the representation of the original clinical data may comprise adding or removing one or more treatment features. For example, the one or more treatment features may comprise: interproximal (IPR) spacing, attachments, bite ramps, hooks, etc. Receiving modifications to the original clinical data may comprise receiving modification of one or more of tooth position and tooth orientation.

Any of these methods may include receiving an original clinical data for a subject's dentition. Receiving modifications to the original clinical data may include receiving modifications to the original clinical data from one or more graphical user interface tools (e.g., virtual buttons, switches, etc.).

All or some of the steps of these methods may be repeated. For example, the methods described herein may include: receiving modifications to the view state of the 3D representation of the modified clinical data, forming a 3D scene of the original clinical data modified by the modifications to the original clinical data, rendering the modified clinical data as the 3D representation based on the 3D scene and view state, displaying the 3D representation of the modified clinical data, and receiving further modifications.

For example, described herein are computer-implemented methods including: displaying a representation of an original clinical data for a subject's dentition; receiving modifications to the original clinical data, wherein the modifications comprise changes in one or more of tooth position and tooth orientation; receiving modifications to a view state of the representation of the original clinical data, including adding or removing one or more treatment features; forming a 3D scene of the original clinical data modified by the modifications to the original clinical data; rendering the modified clinical data as a 3D representation based on the 3D scene and view state; displaying the 3D representation of the modified clinical data; and receiving further modifications to the original clinical data after displaying the 3D representation of the modified clinical data and updating the 3D scene, view state and 3D representation of the modified clinical data after receiving the further modification of the original clinical data.

Any of these methods may be particularly effective for use in systems in which part of the processing is occurring remotely (e.g., on a remote processor). For example, the steps of displaying the representation of the original clinical data for a subject's dentition, receiving modifications to the original clinical data, and receiving modifications to a view state of the representation of the original clinical data may be performed at a web client (e.g., a local processor), while the steps of forming the 3D scene of the original clinical data modified by the modifications to the original clinical data and rendering the modified clinical data as the 3D representation based on the 3D scene and view state may be performed at a remote site (e.g., a remote processor).

Any of the methods (and any associated steps of the method) may be performed by a system. For example, in general a system may include one or more processors and a memory coupled to the processor holding computer-implemented program instructions for performing the computer-implemented method on the one or more processors. For example, a system (e.g., for modifying or designing a orthodontic treatment plan) may include: one or more processors; and a memory coupled to the one or more processors, the memory configured to store computer-program instructions, that, when executed by the one or more processors, perform a computer-implemented method comprising: displaying a representation of an original clinical data for a subject's dentition; receiving modifications to the original clinical data; receiving modifications to a view state of the representation of the original clinical data; forming a 3D scene of the original clinical data modified by the modifications to the original clinical data; rendering the modified clinical data as a 3D representation based on the 3D scene and view state; displaying the 3D representation of the modified clinical data; and receiving further modifications to the original clinical data after displaying the 3D representation of the modified clinical data and updating the 3D scene, view state and 3D representation of the modified clinical data after receiving the further modification of the original clinical data.

Also described herein are methods of displaying, condensing, storing and reconstructing collision regions between two or more teeth.

For example, a computer-implemented method (e.g., for reviewing and/or identifying collisions in an orthodontic treatment plan) may include: determining, from a three-dimensional (3D) digital model of a subject's dentition, one or more regions of occlusion between teeth in the digital model of the subject's dentition; generating a representation of each identified region of occlusion, the representation comprising an indicator of the depth of the occlusion, and an outline of the region of occlusion relative to a surface of the 3D digital model, wherein the outline comprises a plurality of guidepoints; and reducing the representation of each region of occlusion by reducing a number of guidepoints in each representation of the region of occlusion.

Any of these methods may include identifying mirrored pairs of regions of occlusions from the one or more regions of occlusion, and removing one of the regions of occlusions from each mirrored pair, and marking a remaining one of the regions of occlusions from each mirrored pair as mirrored. For example, an occlusion between two teeth may be the same on both teeth; thus the methods and systems described herein may identify just one of the collision regions and indicate that a corresponding collision region may be found on the corresponding (e.g., adjacent or opposite) tooth.

The 3D digital model of the subject's dentition may comprise both the subject's upper and/or lower arch.

Any of the methods described herein may include saving the representations of the occlusions as file associated with the digital model of the subject's dentition. This file may be stored, transmitted and/or used to display the one or more collisions/occlusions. Alternatively or additionally, the representations of the occlusions may be included with the 3D representation (e.g., digital model) of the subject's teeth, including a modified version of the 3D representation, showing a possible treatment plan.

The digital model of the subject's dentition may comprises a digital model in which the subject's tooth position has been modified from a clinical position of the subject's tooth position.

In general, the guidepoints may include one or more of: points, splines, vertices, or vectors. The guidepoints may be compressed, to minimize the number of guidepoints and to optimize the small file sizes.

Any of the methods described herein may include displaying the identified regions of occlusions on the 3D digital model of the subject's dentition using the reduced representation of each region of occlusion. The methods described herein may include determining a color for the display of the reduced representation of each region of occlusion based on a threshold of the depth of occlusion for each region of occlusion. For example, more serious collisions may be represented as red, while less serious collisions may be shown in green or other colors.

Reducing the representation of each region of occlusion may comprise including an indicator of the tooth number on which the region of occlusion is present and/or a reference to the surface region on the tooth or teeth. For example, the methods described herein may include one or more indicators of the tooth, depth of collision (e.g., seriousness of the collision), the location on the tooth (e.g., relative to a coordinate system for the 3D model), which may be included as part of the outline and corresponding guidepoints.

For example, a computer-implemented method may include: determining, from a three-dimensional (3D) digital model of a subject's dentition, one or more regions of occlusion between teeth in the digital model of the subject's dentition; generating a representation of each identified region of occlusion, the representation comprising an indicator of the depth of the occlusion, a tooth number on which the region of occlusion is present, and an outline of the region of occlusion relative to a surface of the 3D digital model, wherein the outline comprises a plurality of guidepoints; reducing the representation of each region of occlusion by reducing a number of guidepoints in each representation of the region of occlusion; and displaying the identified regions of occlusions on the 3D digital model of the subject's dentition using the reduced representation of each region of occlusion.

As mentioned above, also described herein are systems for performing any of these methods. For example, a system for displaying, condensing, storing and reconstructing collision regions between two or more teeth. A system may include: one or more processors; memory coupled to the one or more processors, the memory configured to store computer-program instructions, that, when executed by the one or more processors, perform a computer-implemented method comprising: determining, from a three-dimensional (3D) digital model of a subject's dentition, one or more regions of occlusion between teeth in the digital model of the subject's dentition; generating a representation of each identified region of occlusion, the representation comprising an indicator of the depth of the occlusion, and an outline of the region of occlusion relative to a surface of the 3D digital model, wherein the outline comprises a plurality of guidepoints; and reducing the representation of each region of occlusion by reducing a number of guidepoints in each representation of the region of occlusion.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1B is a schematic of one example of a method for reviewing and/or identifying collisions in an orthodontic treatment plan as described herein.

DETAILED DESCRIPTION

Described herein are methods and apparatuses for handling modifications of clinical orthodontic data. In general, clinical orthodontic data may include data on tooth location as well as information about equipment (e.g., attachments, ramps, etc.) attached to the tooth or teeth and/or information about tooth modifications, such as interproximal reductions, tooth extraction, etc. In some variations, the clinical data may include a series of treatment stages, including the tooth position(s) at each stage and/or rotations of the teeth at each stage. This information may be constructed as a hierarchical description of the subject's jaw, including at the highest level, both upper and lower jaw.

The subject's original clinical data may be displayed as part of a user interface. For example in some variations the user may be shown a 3D 'scene' or model of the teeth, including the changes in the teeth, attachments, etc. This original clinical data may be modified During the planning phase of an orthodontic treatment, the dental/orthodontic professional may modify the teeth, e.g., by operating a user interface to change a control (e.g., pushing a button, selecting via mouse or trackball, hand-selected regions, etc.) through the user interface. The user interface may contact and/or communicate with the original clinical data and/or may modify the 3D tooth model by directly manipulating the position of the teeth, the attachments, space between teeth, interproximal reduction (IPR), etc. The modification may also be made through a user interface control. A modification may be in one or many of the stages of the treatment plan. Such modifications may be referred to herein as "modified clinical data". More specifically, modified clinical data may be changes or selections modifying the clinical data to move the teeth or adjust the teeth. In some variations it would be highly beneficial to have modified clinical data changes to the clinical data (e.g., showing/removing attachments, moving teeth, etc.) be visible immediately and comprehensively across all displays and user interfaces, even for multiple treatment plans. Further, it may be helpful to keep the original clinical data and the modified clinical data, which may be independent data structures, separate since the modified clinical data may be further modified.

Figure 1A:
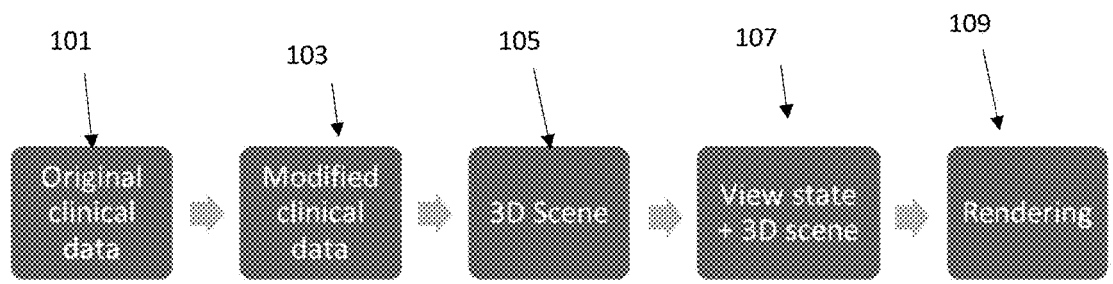
FIG. 1A is a schematic representation of a method of representing user modifications to an orthodontic treatment plan.

FIG. 1A illustrates an example of a method of displaying, quickly and efficiently, changes made to an original clinical set of data describing one or more orthodontic treatment plans by a user (e.g., doctor) operating a user interface. In this example, the original clinical data 101 and the modified clinical data 103 (if any) may be provided to a 3D scene engine 105 that may combine the two with a user interface to form a view state and 3D scene 107. The view state may hold the data regarding the overall view, typically including the user interface, while the 3D scene holds the digital tooth model(s). A rendering engine ("renderer") 109 may then render (draw) the user interface and 3D model of the teeth. The view state may describe how the renderer ultimately renders the image and user interface. The Renderer may also determine when to update the 3D scene, to reflect changes made by the user. Further, the Renderer may modify only part of the hierarchy of the original clinical data, and may apply control logic to determine when and if to regenerate a scene (e.g., display or user interface)

Thus, in practice separate original clinical data may be kept isolated from modified clinical data, and combined to form the 3D scene and view data for display and interaction with the user. In some variations, the modifications held in the modified clinical data may be combined with (and absorbed into) the original claim data.

FIG. 1B shows one example of a computer-implemented method 119 of modifying or designing an orthodontic treatment plan. This exemplary method may include displaying a representation of an original clinical data for a subject's dentition 120. The method may further include receiving modifications to the original clinical data, wherein the modifications comprise changes in one or more of tooth position and tooth orientation 122 and receiving modifications to a view state of the representation of the original clinical data, including adding or removing one or more treatment features 124. As shown in FIG. 1A, a 3D scene of the original clinical data modified by the modifications to the original clinical data may be formed 126. The modified clinical data may be rendered as a 3D representation based on the 3D scene and view state 128. Thereafter, the 3D representation of the modified clinical data may be displayed 130. Further modifications to the original clinical data may be received after displaying the 3D representation of the modified clinical data and updating the 3D scene, view state and 3D representation of the modified clinical data after receiving the further modification of the original clinical data 132.

Figure 2:
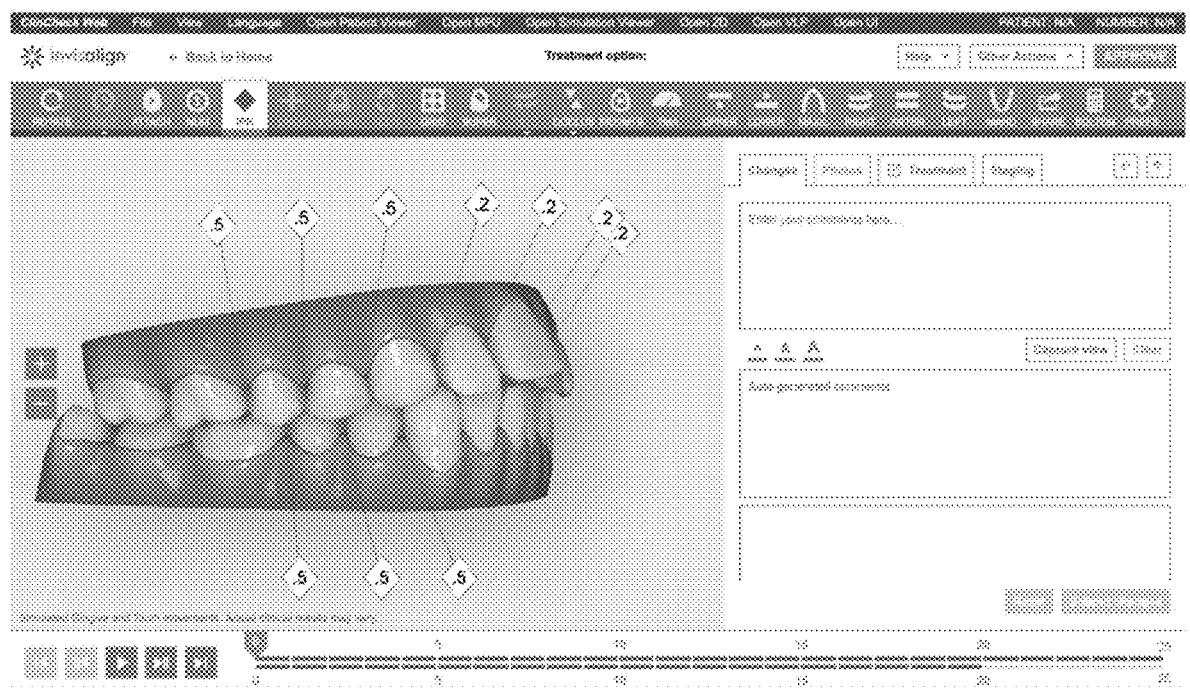
FIG. 2 is an example of an orthodontic treatment plan in a user interface.

FIGS. 2-6 illustrate one example of a methods an apparatuses described herein may be used to display user input or modifications to one or more treatment plan. For example, FIG. 2 illustrates Web used treatment data presentation oriented clinical meaning presentation, technician—doctor communication and modification workflow support. For 3D visual representation a data flow and algorithm such as that illustrated in FIG. 1A may be applied. The base clinical data may be used to create and update a 3D scene presentation, which may be further routed to a renderer for visualization, handling additional visualization parameters (e.g., view state), related to settings and tools used by doctor in each moment of time. In FIG. 2, an initial view is shown, e.g., showing the interpretation of the original clinical data; there is no modification yet (e.g., no modified clinical data). The 3D scene is the combination of the rendered teeth as indicated by the original clinical data and the modifications.

Figure 3:
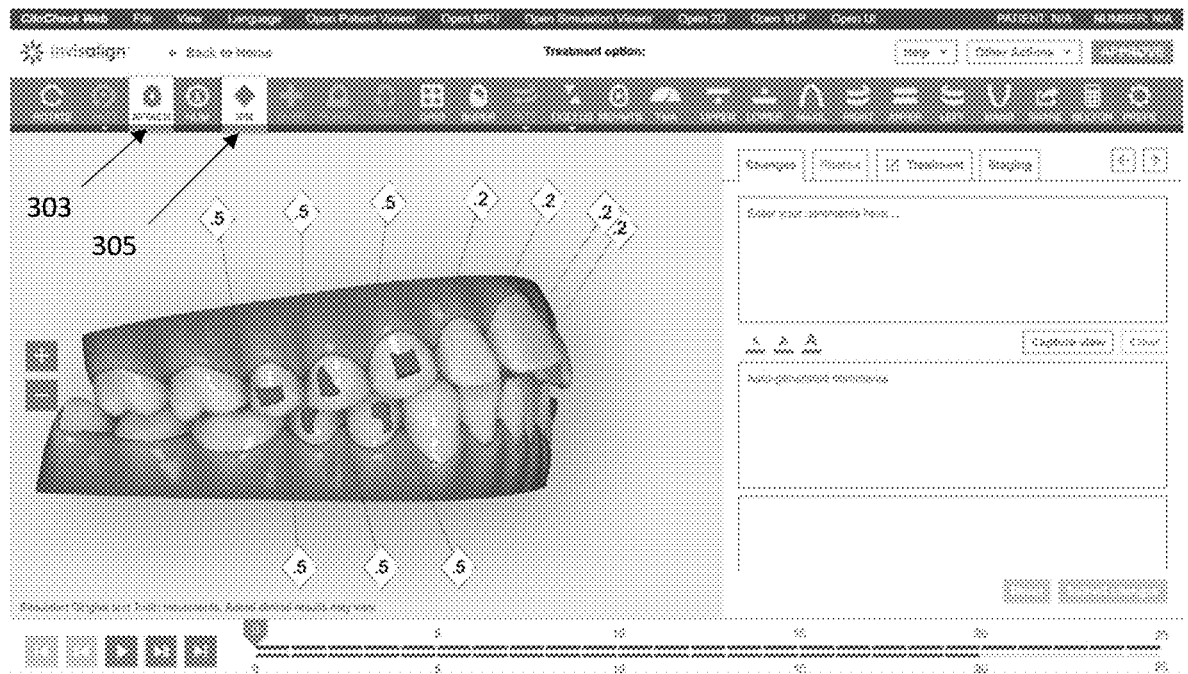
FIG. 3 is an example of a modified version of the treatment plan shown in FIG. 2.
Figure 4:
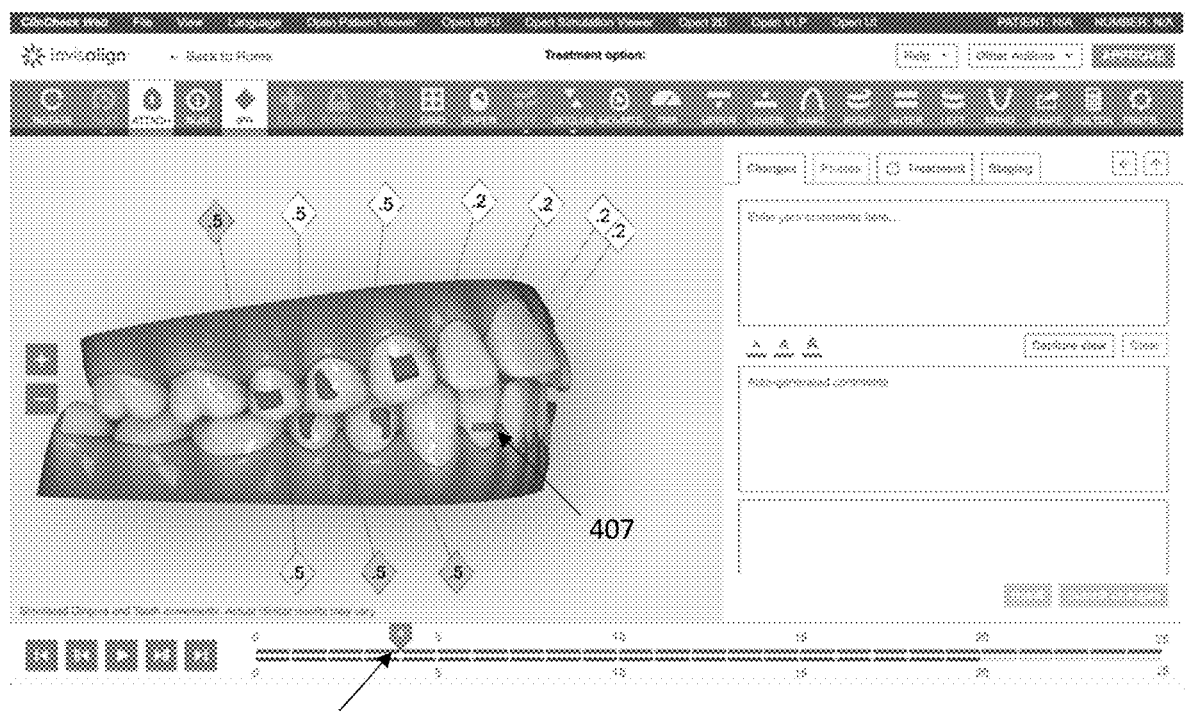
FIG. 4 is an example of a modified version of the treatment plan shown in FIGS. 2 and 3.
Figure 5:
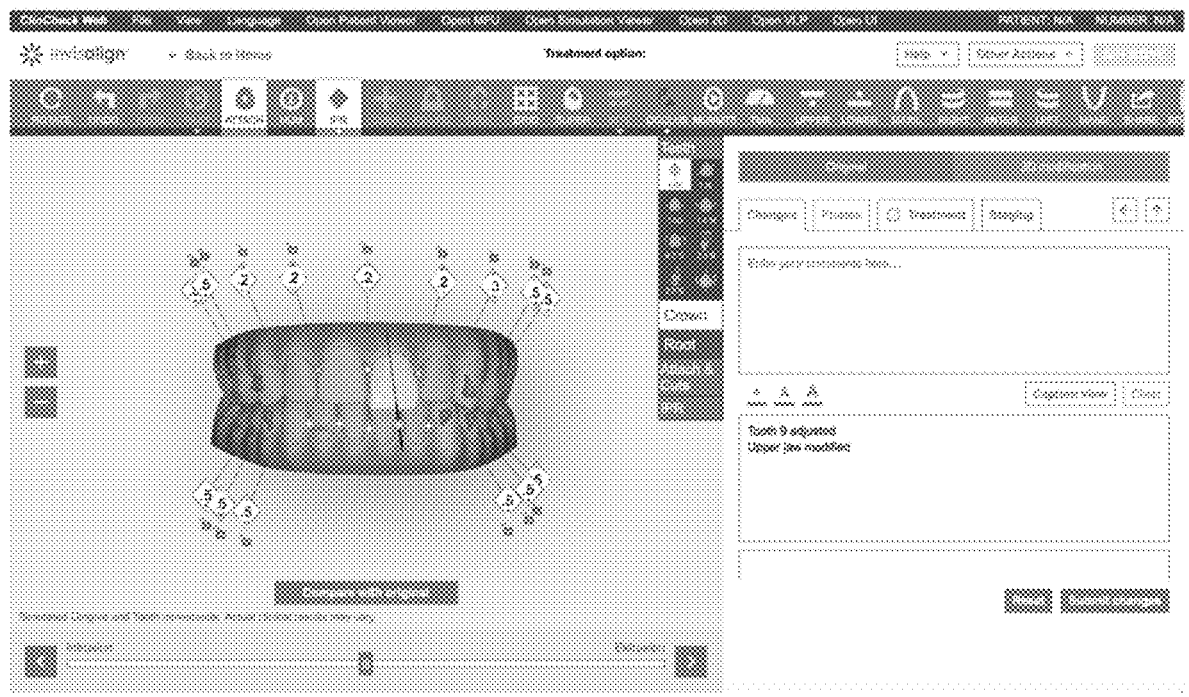
FIG. 5 is an example of another variation of a user interface that is using the same treatment plan and modified clinical data shown in FIGS. 2-4, above.

In FIG. 3, the user interface is used to select one or more changes in the view state. For example, the view state (without any clinical data modified) is shown and the attachments visualization is turned on by selecting the "attachments" control 303 on the user interface interproximal reduction IPR) is also selected 305. These selections may from part of the modified clinical data and may control the display of features (e.g., attachments in this example) from the original clinical data. Thus, in FIG. 3, the view state shows the changed image, although there has been no change to the clinical data (which remains un-modified). In FIG. 4, the user has selected (e.g., by activating a control 405 on the bottom of the user interface, corresponding to the fourth user interface) the o $4^{th}$ stage of a treatment plan for visualization. In this figure, the tooth position is updated to reflect the fourth stage, and the gingiva shape may be updated, the IPR state may be updated, and in addition, a power ridge 407 is also visible.

In FIG. 4 the clinical data has been updated, and the visualization of the updated clinical data (e.g., showing a modification applied to original clinical data) is shown in the view state with a selected tooth with visualization. In the example shown in FIG. 4, the teeth have been moved to show the anterior teeth, and one tooth is selected. Thus, the model of the teeth shows the features previously toggle 'on' by the user (e.g., IPR, attachment), and the new user interface (allowing intrusion/extrusion of the selected tooth) is fully updated accordingly, per FIG. 1. Also in this example, comments made manually or automatically, as well as all of these additional changes to the user interface are reflected in the 3D scene and view state and some of these changes may be updated to the clinical data, and/or they may remain in the modified clinical data.

Occlusion Contacts Shape Reconstruction on Base Outline and Tooth Shape

Also described herein are methods and apparatuses for displaying occlusion shape and reconstruction of the occlusion using a base outline and a tooth shape. It may generally be valuable to identify and store inter-arch occlusion contacts. Inter-arch occlusion contact are one important clinical parameter for treatment; this clinical parameter should be visualized for review by the doctor or other dental practitioner (e.g., dentist, orthodontist, etc.). Collision information may be provided to the user when proposing one or more change in the tooth alignment, e.g., during treatment planning to automatically or manually describe a set of tooth movements as part of the treatment planning. For example, a user (e.g., a doctor) may move one or more teeth, which may directly or indirectly lead to collisions. Visualizing collisions may also help further in the design of a treatment plan that may display occlusion contacts at the end of treatment proposed automatically and/or manually, as well during 3D modification done by user.

In general, saving occlusion contacts data as 3D shape can lead to significant growth of file and file size with treatment. This may result in inefficiencies that will extend loading time of treatment in doctor application for review. This may also be the case when updating occlusion contacts during modification with interactive 3D tools. In practice, a collision may be detected between two or more teeth in any appropriate manner. Once detected, the region of collision may be modeled. In general, the modeling may be done by modeling the collision region using a standard mesh model, including vertices and triangular-shaped region. Unfortunately such modeling is time and size intensive. Described herein are methods in which the collision region may instead by simplified, modeled as a projection of a surface, and stored in a reduced format that requires much less space and calculation time. For example, in one variations, updated collision data is created on the back end, and transferred plain 3D shape to be sent to the client may take significant time and will reduce interactivity of modifications.

For example, in some variations, the collision region may be modeled by a projection of a flat surface onto the tooth surface by a point source (e.g., a light source) that is at a particularly distance and location from the tooth, with the shape between the light source and the tooth and also at a known distance and position. Prior to modeling the collision region in this manner, the region of collision may first be simplified. This may be done by reducing the number of vertices and/or edge regions. Once reduced to a simpler form, the second part of the modeling may performed, solving to get a flat surface at an identified location in space with a point light source behind it. Once identified, the simplified model may be stored, and later used to reconstruct the collisions (e.g., when displaying the treatment plan or a model of the subject's teeth.

Figure 6:
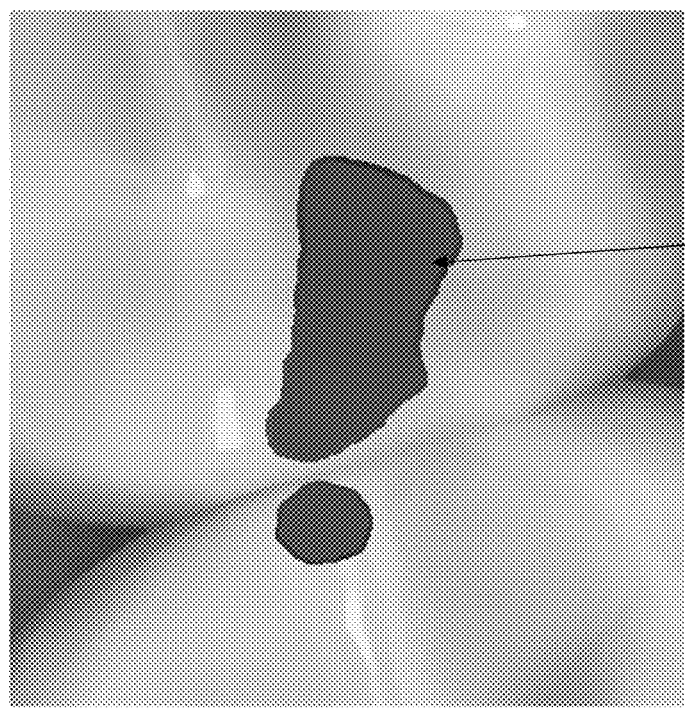
FIG. 6 is an example showing a collision region that may be modeled, stored and reconstructed in the simplified method described herein.

FIG. 6 shows one example of a collision region 805. Occlusion contacts represented by outline splines in a treatment file may be output as of computing backend during 3D modification. Described herein is a method and apparatus for restoring the shape (e.g., 3D shape) of an occlusion contact between two teeth, and visualizing it so that the doctor using provided outline and shape of tooth where contact appear using graphics card acceleration (OpenGL, WebGL).

In general, the methods described herein may be collapsed down into a contour, rather than a full shape, and the contour may be stored in a much smaller form, reducing the size and complexity of the collision region. For example, the method described herein may represent occlusion data as a spline of the outer outline of each contact of the collision, and the methods described herein may reduce the complexity of this spline keeping enough data to allow precise restoring initial contact shape on the client. For example, as mentioned above, when encoding the collision region a 2D shape is identified that would result in the shape of the collision region on/between the teeth when a light source (e.g., modeled to emit parallel beams of 'light') that cast a shadow the shape of the collision region. The collision region may be simplified (e.g., lightly decimated) prior to modeling by the 2D surface (contour) and light source. The resulting 2D contour shape as well as the orientation of the light source and shape in space may then be transmitted/ stored to represent the collision region. During operation of system, e.g., showing the final position of the teeth following a proposed treatment plan, the collision region may be constructed from this compact form.

Figure 7:
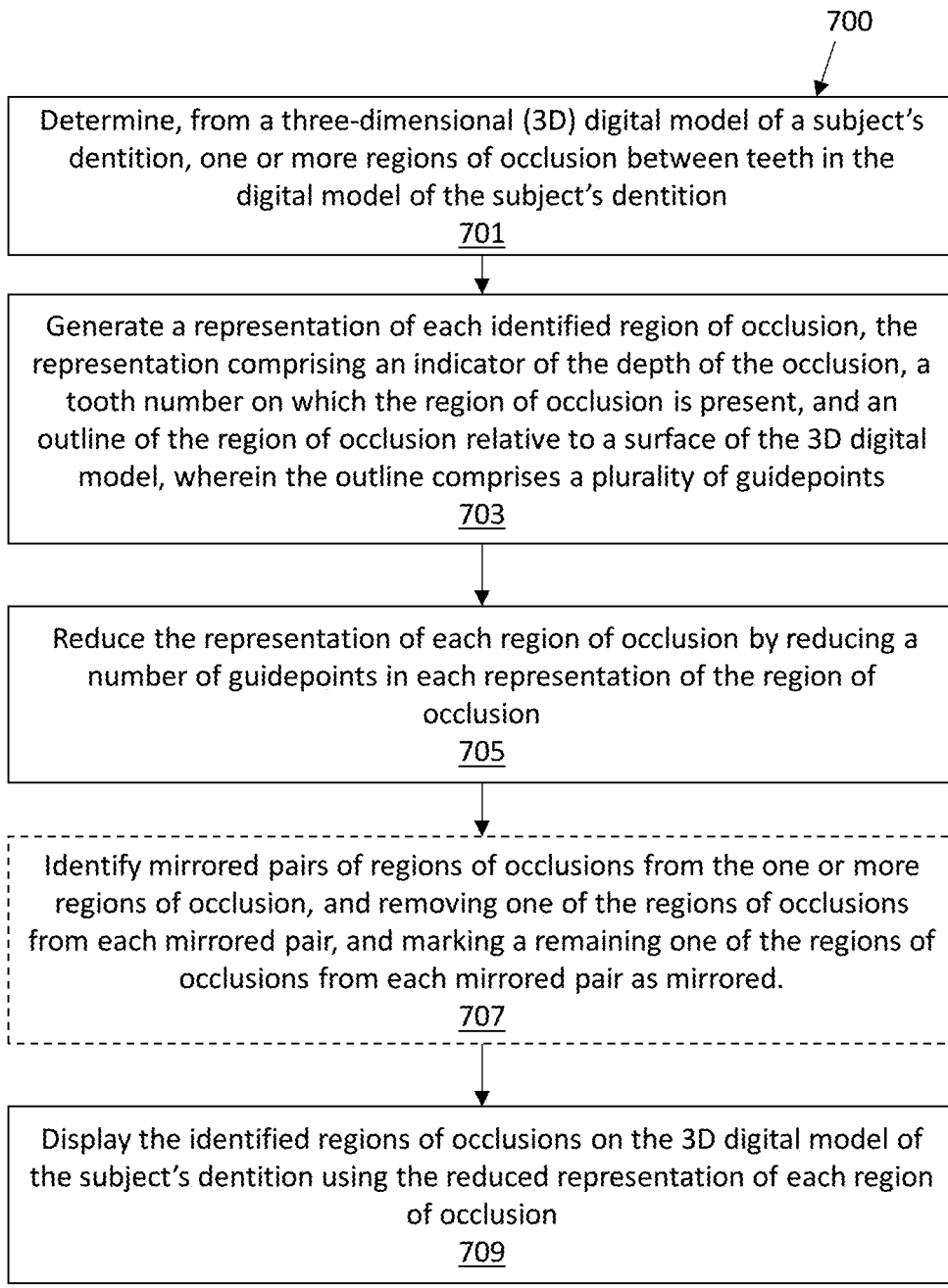
FIG. 7 is an example of a method for identifying and efficiently storing for later display and/or use regions of collision between teeth during an after an orthodontic (or dental) process.

FIG. 7 illustrates one method 700 of a method for identifying and efficiently storing for later display and/or use regions of collision between teeth during an after an orthodontic (or dental) process. In FIG. 7, the method may include determining, from a three-dimensional (3D) digital model of a patient's dentition, one or more regions of occlusion between teeth in the digital model of the patient's dentition 701. A representation of each identified region of occlusion may generated 703, the representation comprising an indicator of the depth of the occlusion, a tooth number on which the region of occlusion is present, and an outline of the region of occlusion relative to a surface of the 3D digital model, wherein the outline comprises a plurality of guidepoints. In some variations the representation does not include the depth of the collision. The method may also include reducing the representation of each region of occlusion by reducing a number of guidepoints in each representation of the region of occlusion 705. Optionally, the method may include identifying mirrored pairs of regions of occlusions from the one or more regions of occlusion, and removing one of the regions of occlusions from each mirrored pair, and marking a remaining one of the regions of occlusions from each mirrored pair as mirrored 707. Finally, the method may include displaying the identified regions of occlusions on the 3D digital model of the patient's dentition using the reduced representation of each region of occlusion 709.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc.

Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The invention claimed is:

1. A computer-implemented method, the method comprising:
   determining, from a three-dimensional (3D) digital model of a subject's dentition, one or more regions of occlusion between teeth in the digital model of the subject's dentition;
   generating a representation of each identified region of occlusion, the representation comprising an indicator of a depth of the occlusion, and an outline of the region of occlusion relative to a surface of the 3D digital model, wherein the outline comprises a plurality of guidepoints;
   reducing the representation of each region of occlusion by reducing a number of guidepoints in each representation of the region of occlusion; and
   identifying mirrored pairs of regions of occlusions from the one or more regions of occlusion and removing one of the regions of occlusions from each mirrored pair, and marking a remaining one of the regions of occlusions from each mirrored pair as mirrored.

2. The method of claim 1, wherein the 3D digital model of the subject's dentition comprises both the subject's upper and lower arch.

3. The method of claim 1, further comprising saving the representations of the regions of occlusion as a file associated with the digital model of the subject's dentition.

4. The method of claim 1, wherein the digital model of the subject's dentition comprises a digital model in which the subject's tooth position has been modified from a clinical position of the subject's tooth position.

5. The method of claim 1, wherein the guidepoints comprises one or more of:
   points, splines, vertices, or vectors.

6. The method of claim 1, further comprising displaying the identified regions of occlusions on the 3D digital model of the subject's dentition using the reduced representation of each region of occlusion.

7. The method of claim 6, further comprising determining a color for the display of the reduced representation of each region of occlusion based on a threshold of the depth of the occlusion for each region of occlusion.

8. The method of claim 1, wherein reducing the representation of each region of occlusion comprises an indicator of a tooth number on which the region of occlusion is present.

9. A computer-implemented method, the method comprising:
   determining, from a three-dimensional (3D) digital model of a subject's dentition, one or more regions of occlusion between teeth in the digital model of the subject's dentition;
   generating a representation of each identified region of occlusion, the representation comprising an indicator of a depth of the occlusion, a tooth number on which the region of occlusion is present, and an outline of the region of occlusion relative to a surface of the 3D digital model, wherein the outline comprises a plurality of guidepoints;
   reducing the representation of each region of occlusion by reducing a number of guidepoints in each representation of the region of occlusion;
   identifying mirrored pairs of regions of occlusions from the one or more regions of occlusion, and removing one of the regions of occlusions from each mirrored pair, and marking a remaining one of the regions of occlusions from each mirrored pair as mirrored; and
   displaying the identified regions of occlusions on the 3D digital model of the subject's dentition using the reduced representation of each region of occlusion.

10. The method of claim 9, wherein the 3D digital model of the subject's dentition comprises both the subject's upper and lower arch.

11. The method of claim 9, further comprising saving the representations of the regions of occlusion as a file associated with the digital model of the subject's dentition.

12. The method of claim 9, wherein the digital model of the subject's dentition comprises a digital model in which the subject's tooth position has been modified from a clinical position of the subject's tooth position.

13. The method of claim 9, wherein the guidepoints comprises one or more of:

points, splines, vertices, or vectors.

14. The method of claim 13, further comprising determining a color for the display of the reduced representation of each region of occlusion based on a threshold of the depth of the occlusion for each region of occlusion.

15. A system comprising:

one or more processors;

memory coupled to the one or more processors, the memory configured to store computer-program instructions, that, when executed by the one or more processors, perform a computer-implemented method comprising:

determining, from a three-dimensional (3D) digital model of a subject's dentition, one or more regions of occlusion between teeth in the digital model of the subject's dentition;

generating a representation of each identified region of occlusion, the representation comprising an indicator of a depth of the occlusion, and an outline of the region of occlusion relative to a surface of the 3D digital model, wherein the outline comprises a plurality of guidepoints;

reducing the representation of each region of occlusion by reducing a number of guidepoints in each representation of the region of occlusion; and identifying mirrored pairs of regions of occlusions from the one or more regions of occlusion, and removing one of the regions of occlusions from each mirrored pair, and marking a remaining one of the regions of occlusions from each mirrored pair as mirrored.

* * * * *